United States Patent [19]

Taran et al.

[11] Patent Number: 6,070,466
[45] Date of Patent: Jun. 6, 2000

[54] DEVICE FOR ULTRASONIC INSPECTION OF A MULTI-LAYER METAL WORKPIECE

[75] Inventors: Vladimir Taran, Jerusalem; Kenneth Jassby, Herzlia; Stella Muchnik, Jerusalem; Oz Vachtenberg, Tel-Aviv, all of Israel

[73] Assignee: Scanmaster Systems (IRT) Ltd., Israel

[21] Appl. No.: 09/076,576

[22] Filed: May 12, 1998

[30] Foreign Application Priority Data

May 14, 1997 [IL] Israel ........................................ 120830

[51] Int. Cl.⁷ .......................... G01N 29/06; G01N 29/10; G01N 29/24
[52] U.S. Cl. ................................ 73/622; 73/620; 73/627; 73/628
[58] Field of Search ............................... 73/579, 582, 597, 73/598, 602, 609, 614, 615, 616, 627, 629, 599, 600, 622, 624, 625, 628, 623, 617, 620, 644

[56] References Cited

U.S. PATENT DOCUMENTS

| 2,784,325 | 3/1957 | Halliday et al. ........................... 73/628 |
| 3,100,987 | 8/1963 | Bincer ....................................... 73/641 |
| 4,398,421 | 8/1983 | White ........................................ 73/597 |
| 4,484,475 | 11/1984 | Ogura et al. . | |
| 4,712,428 | 12/1987 | Ishii et al. ................................. 73/644 |
| 5,201,225 | 4/1993 | Takahashi et al. . | |
| 5,349,860 | 9/1994 | Nakano et al. ............................ 73/597 |
| 5,431,054 | 7/1995 | Reeves et al. . | |
| 5,992,235 | 11/1999 | Fischer et al. ............................. 73/617 |

FOREIGN PATENT DOCUMENTS 34 41 894  7/1986  Germany .
1 266 342  3/1972  United Kingdom .

OTHER PUBLICATIONS

Soviet Journal of Nondestructive Testing—vol. 22, No. 3, Mar. 1986, pp. 157–160—"Thickness Measurement of Objects Having Variable Sound Velocity with Depth Without a Standard".

Primary Examiner—Daniel S. Larkin
Assistant Examiner—Rose M. Miller
Attorney, Agent, or Firm—Anthony J. Casella; Gerald E. Hespos; Michael J. Porco

[57] ABSTRACT

The invention provides a device for the ultrasonic inspection of a multilayer metal workpiece consisting of at least one parent metal layer and a clad metal layer, and having an outer surface, at least one boundary surface, and an inner surface, the device comprising a housing accommodating at least three spaced-apart, ultrasonic transducing means capable of receiving electrical input signals, initiating transmission of ultrasonic waves to the workpiece, and receiving reflected ultrasonic waves to be transduced into electrical output signals, the transducing means being constituted by an acoustic prism having a first face for at least indirectly contacting a workpiece, a second face extending in a plane forming an angle α with the plane of the outer surface of the workpiece, and a piezocrystal attached to the second face, wherein the distance $L_2$ between the points where the acoustic axes of each of the second and the third spaced-apart transducing means of the three spaced-apart transducing means traverses the first face of its acoustic prism, is determined by the expression $L_2 = K \cdot 2 \, h \cdot \tan d$, wherein K is a coefficient indicating the number of skips of the shear wave reflection from the inner surface of the workpiece, and h is the mean thickness of the clad metal layer.

9 Claims, 7 Drawing Sheets

DEVICE FOR ULTRASONIC INSPECTION OF A MULTI-LAYER METAL WORKPIECE

FIELD OF THE INVENTION

The present invention relates to the field of ultrasonic inspection of metal workpieces, and more particularly to a device for ultrasonic inspection of a multi-layer, clad metal, bonded construction workpiece. The invention is utilizable in quality control of the bonding of two metals (parent or mother clad metal boundary) and in control of the clad metal thickness. Bonding may be effected by a metallurgical welding of the parent to clad material, or by solid solution mixtures which form a strong atomic bonding at the interface layer.

BACKGROUND OF THE INVENTION

The ultrasonic quality control of double-layer bonded construction of a workpiece is of great industrial importance. An example of such a workpiece is a tube made of low carbon or low alloyed steel (parent metal) with a thin layer of stainless steel (clad metal) clad on the tube's internal or external surface.

Quality control and control of clad metal thickness are usually solved by means of direct, single or dual ultrasonic probes, as disclosed, e.g., in U.S. Pat. No. 5,349,860, filed Sep. 27, 1994, entitled "Apparatus for Measuring the Thickness of Clad Material." The apparatus provides control of the bonding quality at the boundary of two metals by means of registration of the amplitude of the echo signal reflected from the boundary, however with low sensitivity, because of the low amplitude of echo signals reflected from the boundary, making it difficult to detect defects in the bonding. The apparatus further provides control of the clad metal thickness, but with low precision because of the weak level (amplitude) of the ultrasonic signal reflected or refracted from the bonded interface. In fact, the angle of propagation of the echo signal B in a material under control is determined by the parameters of the transmitter and by the receiver's angle-type probes, while the angle of the echo signal C is additionally determined by the clad metal thickness. Therefore, the time of propagation of the echo signal B from the transmitter to the receiver's piezo crystals ($t_b$) is directly proportional to the total thickness of a material (mother clad metal), whereas the time of propagation ($t_1$) of the echo signal C is not directly proportional to the parent metal thickness. Hence, the difference in the propagation times of the echo signals B and C is not directly proportional to the clad metal thickness, but is considerably smaller than its real value. This leads to a large error in measuring the clad metal thickness.

SUMMARY OF THE INVENTION

It is therefore a broad object of the present invention to provide a device for ultrasonic inspection of a multi-layer metal workpiece, ameliorating the above-mentioned drawback of the probe utilized in the prior art apparatus for measuring the thickness of the clad material.

It is a further object of the present invention to provide a device for ultrasonic inspection of a multi-layer metal workpiece, utilizing a novel arrangement of transducing means composed of acoustic prisms and piezocrystals.

It is a still further object of the present invention to provide an unique transducing means consisting of an acoustic prism and a piezocrystal.

Another object of the invention is to provide a single device for ultrasonic inspection of a multi-layer metal workpiece, capable of transmitting both shear waves as well as longitudinal waves into the workpiece, and for receiving reflected echo waves from the workpiece.

In accordance with the present invention, there is therefore provided a device for the ultrasonic inspection of a multilayer metal workpiece consisting of at least one parent metal layer and a clad metal layer, and having an outer surface, at least one boundary surface, and an inner surface, said device comprising a housing accommodating at least three spaced-apart, ultrasonic transducing means capable of receiving electrical input signals, initiating transmission of ultrasonic waves to said workpiece, and receiving reflected ultrasonic waves to be transduced into electrical output signals, said transducing means being constituted by an acoustic prism having a first face for at least indirectly contacting a workpiece, a second face extending in a plane forming an angle α with the plane of the outer surface of said workpiece, and a piezocrystal attached to said second face, wherein the distance $L_2$ between the points where the acoustic axes of each of the second and the third spaced-apart transducing means of said three spaced-apart transducing means traverses the first face of its acoustic prism, is determined by the expression $L_2 = K \cdot 2 \; h \cdot \tan\alpha$, where K is a coefficient indicating the number of skips of the shear wave reflection from the inner surface of said workpiece, and h is the mean thickness of said clad metal layer.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF PREFERRED EMBODIMENTS

Figure 1:
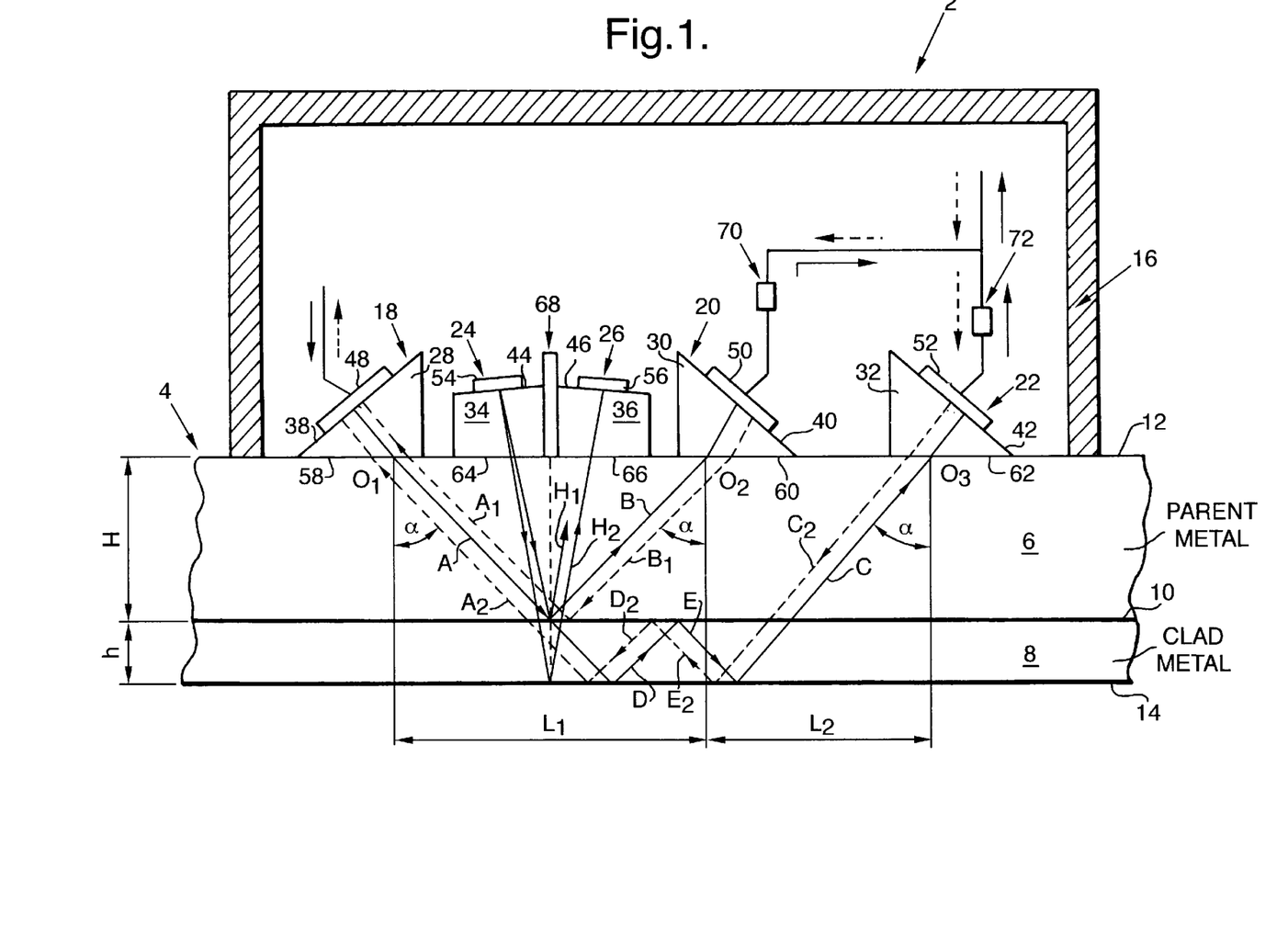
FIG. 1 is a cross-sectional view of the device according to the present invention, generally showing the direction of wave propagation and directions of propagation of reflected or refracted waves from the clad metal of a workpiece.

Referring to FIG. 1, there is illustrated a device 2 for performing ultrasound inspection of a workpiece 4, composed of a first parent metal layer 6 having a thickness H, and a second, clad metal layer 8 of a thickness h. The two layers contact each other along a boundary surface 10. The workpiece 4 may be of any shape or configuration, e.g., composed of two contacting, plate-shaped layers, or it may be in the form of a tube or pipe. The exposed surface of the parent layer will be referred to as "outer surface 12," while the exposed surface of the clad metal layer 8 will be referred to as "inner layer 14," although, in practice, the positions of parent and clad layers may be reversed.

The device 2, which may assume any convenient configuration, is generally constituted by a housing 16 accommodating a plurality of ultrasonic transducing means 18, 20, 22, spaced apart at distances $L_1$ and $L_2$, respectively, and optionally, also transducing means 24 and 26. Each of the transducing means includes an acoustic prism 28, 30, 32 and 34, 36, made of any suitable material and configured to have a first face, respectively 38, 40, 42 and 44, 46, to the surfaces of which are glued or otherwise affixed piezocrystals 48, 50, 52 and 54, 56, and a second face 58, 60, 62 and 64, 66. The second faces are shaped and oriented with respect to housing 16 so as to make at least indirect, intimate contact with the outer surface 12 of workpiece 4.

For the sake of clarity, the electrical leads connecting the piezocrystals to a per se known amplification and processing means, are not shown. However, as indicated by the arrowed full and hatched lines, the transducer means are adapted both to transmit signals to the workpiece 4 and to receive echo, reflected or refracted signals therefrom, as will be described in detail hereinafter.

As further seen in the figures, the angle $\alpha$ of transmission (and reflection) of the acoustic signals with respect to the outer surface 12 of workpiece 4, is determined by the first faces 38, 40, 42 and 44, 46 of the acoustic prisms to which the piezocrystals are affixed, which faces are selected with respect to the measuring considerations. The transducing means and other components are affixed inside housing 2 by any known means, such as epoxy.

As described above, the device 2 also optionally includes transducing means 24, 26 separated by an acoustic screen 68, for detecting bonding or other defects at the boundary surface 10 of the two metals.

The juxtaposed transducing means 24, 26, for transmitting and receiving longitudinal waves, are located between the transducing means 18 and 20, which transmit and receive shear waves. The axis of symmetry of the transducing means 24, 26 and the acoustic axes, as determined by the faces 44, 46, intersect at the same point that the acoustic axes of transducing means 18 and 20 intersect, at the boundary surface 10 of the two metals.

The distance $L_1$ between points $O_1$ and $O_2$, which the acoustic axes of transducing means 18 and 20 transverse the outer surface 12 of workpiece 4 or the faces 58, 60, is calculated by the expression:

$$L_1 = 2\ H \cdot \tan\alpha$$

and similarly, the distance $L_2$ between points $O_2$ and $O_3$ which the acoustic axes of transducing means 20 and 22 transverse the inner surface 14 of workpiece 4 or the faces 60, 62, is calculated by the expression:

$$L_2 = K \cdot 2\ h \cdot \tan\alpha$$

wherein:

H is the thickness of the mother metal;
h is the thickness of the clad metal;
$\alpha$ is the angle of the shear wave propagation; and
K is the reflection coefficient, its value being equal to the number of skips of the shear wave from the inner surface of the workpiece.

These distances provide optimal conditions for receiving the echo signals reflected from the boundary surface of the two metals, due to the different values of the acoustic impedance, and the signals reflected from the inner surface of the workpiece.

The device according to the present invention, and the method of performing measurements therewith, are based on physical differences in reflection of longitudinal and shear waves from the parent/clad metal boundary surface, due to the different acoustic impedance of the two metals. The shear wave gives a high level of the echo signal reflected from the boundary surface 10, but it cannot be used efficiently to simultaneously detect small defects. The longitudinal wave gives a high level of echo signal, even from small defects, but not from the boundary surface 10 for well-bonded material of similar acoustic impedances, and therefore, in many cases, it cannot be used for measuring the clad metal thickness.

Figure 2:
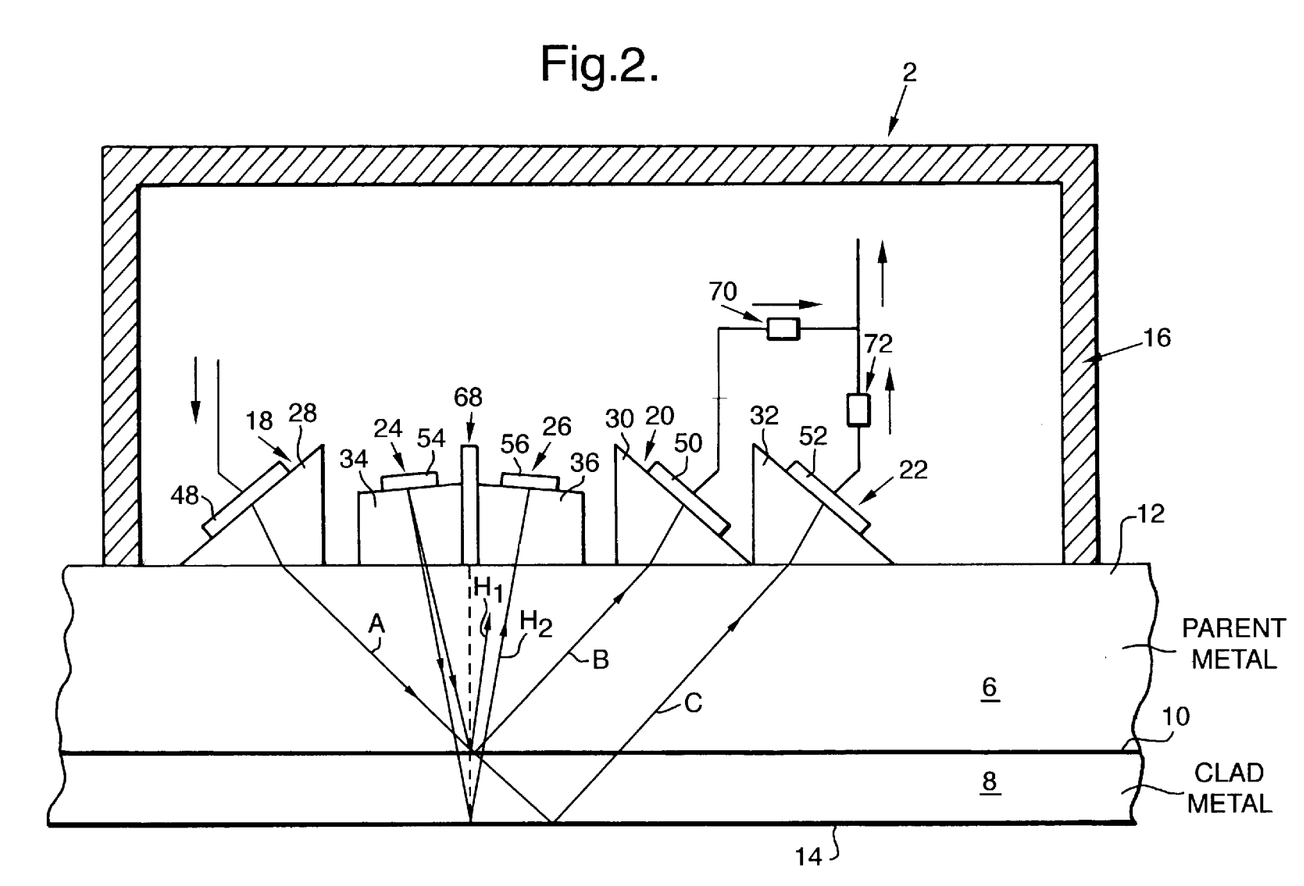
FIG. 2 is a cross-sectional view of a first embodiment of the device according to the present invention and the mode of performing measurements therewith.

Turning now to FIG. 2, there is seen the device 2 as operated in a first mode, in which the transducing means 18 emits shear waves via the parent metal layer 6 to the inner surface 14 of the clad metal layer 8. Both transducing means 20, 22 receive the echo signals, transducer means 20 receiving echo signal B reflected from the boundary surface 10 and transducer means 22 receiving echo signal C reflected from the outer surface 14. In this case, K=1 and the distance $L_1=2$ h·tan$\alpha$. The piezocrystals 50 and 52 are advantageously connected in parallel through means 70, 72 for electronic signal amplification with programmable time variable gain, serving to selectively amplify and level the echo signals B and C reflected from the boundary surface 10 and the inner surface 14 of the workpiece 4.

Figure 3:
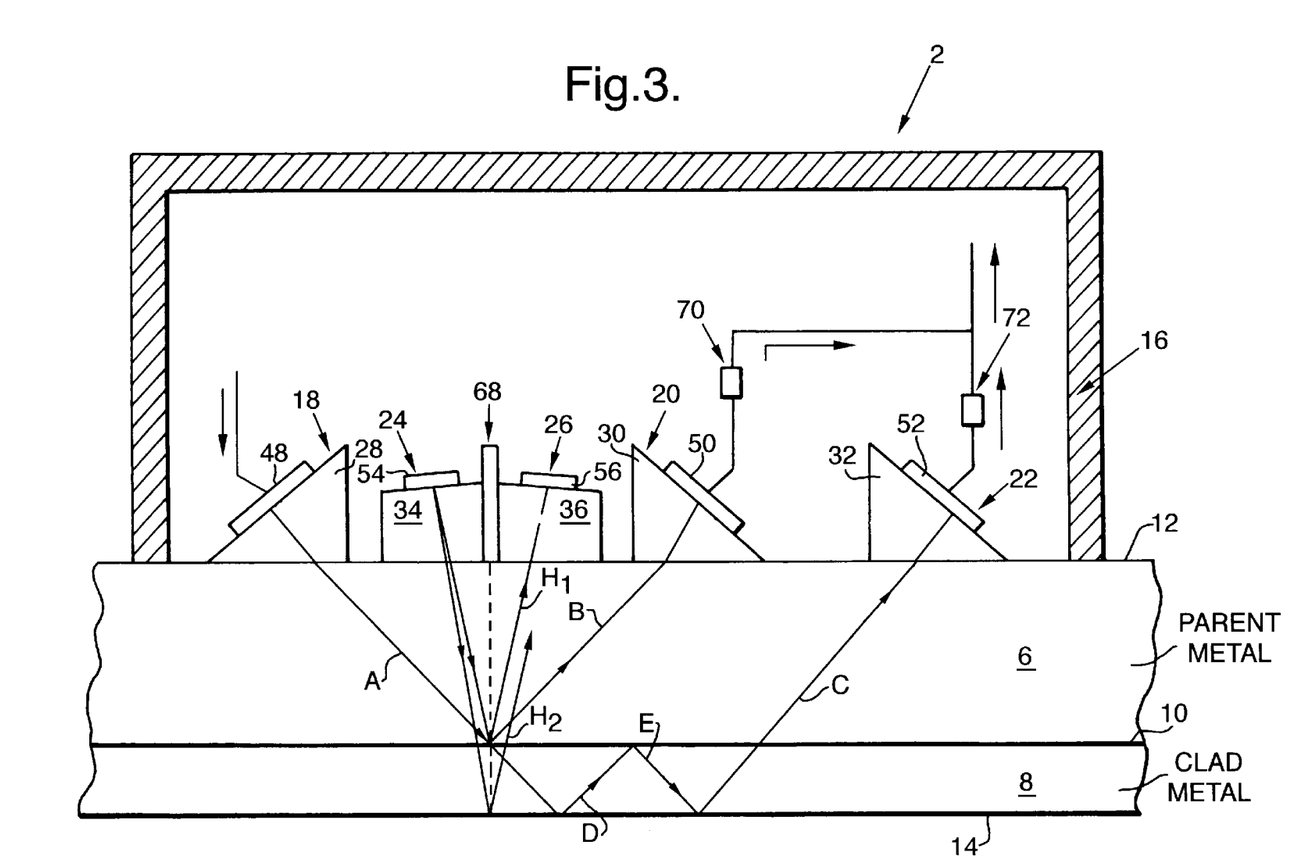
FIG. 3 is a cross-sectional view of a second embodiment of the device according to the present invention and the mode of performing measurements therewith.

FIG. 3 illustrates a version of operation according to which, in contrast to the version of FIG. 2, the transducing means 22 receives echo signals which, after reflection of wave A from the inner surface 14 of echo signal D, impinges on the boundary surface 10 of the two metals. Echo signals are then reflected from this boundary surface (echo signal E), impinges again on the inner surface 14 of the workpiece 4, and then, after reflection from this surface (second reflection), echo signal C reaches receiving transducing means 22. In this case, K=2 and the distance $L_2=4$ h·tan$\alpha$.

Figure 4:
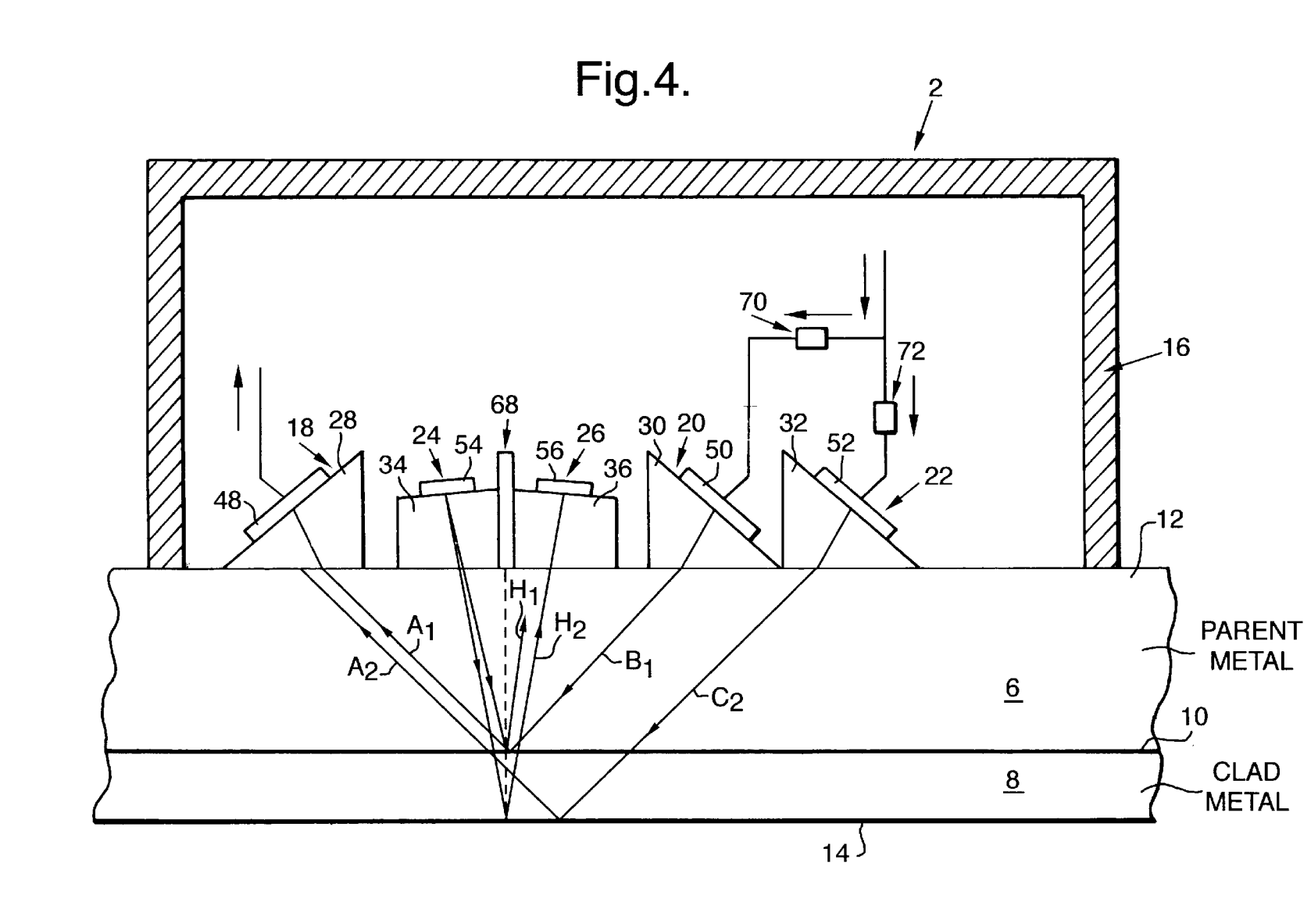
FIG. 4 is a cross-sectional view of a further embodiment of the device according to the present invention and the mode of performing measurements therewith.

In FIG. 4, there is illustrated an embodiment in which the transducing means 20, 22 emit shear waves $B_1$ and $C_2$ in the direction of clad metal layer 8 from the direction of the outer surface 12 of the workpiece. The transducing means 18 receives two echo signals $A_1$ and $A_2$, the first echo signal $A_1$ being reflected from the boundary surface 10 of the two metals when wave $B_1$ impinges thereon; the second echo signal $A_2$ being reflected from the inner surface 14 when wave $C_2$ impinges thereon. In this case, K=1 and the distance $L_2=2$ h·tan$\alpha$.

Figure 5:
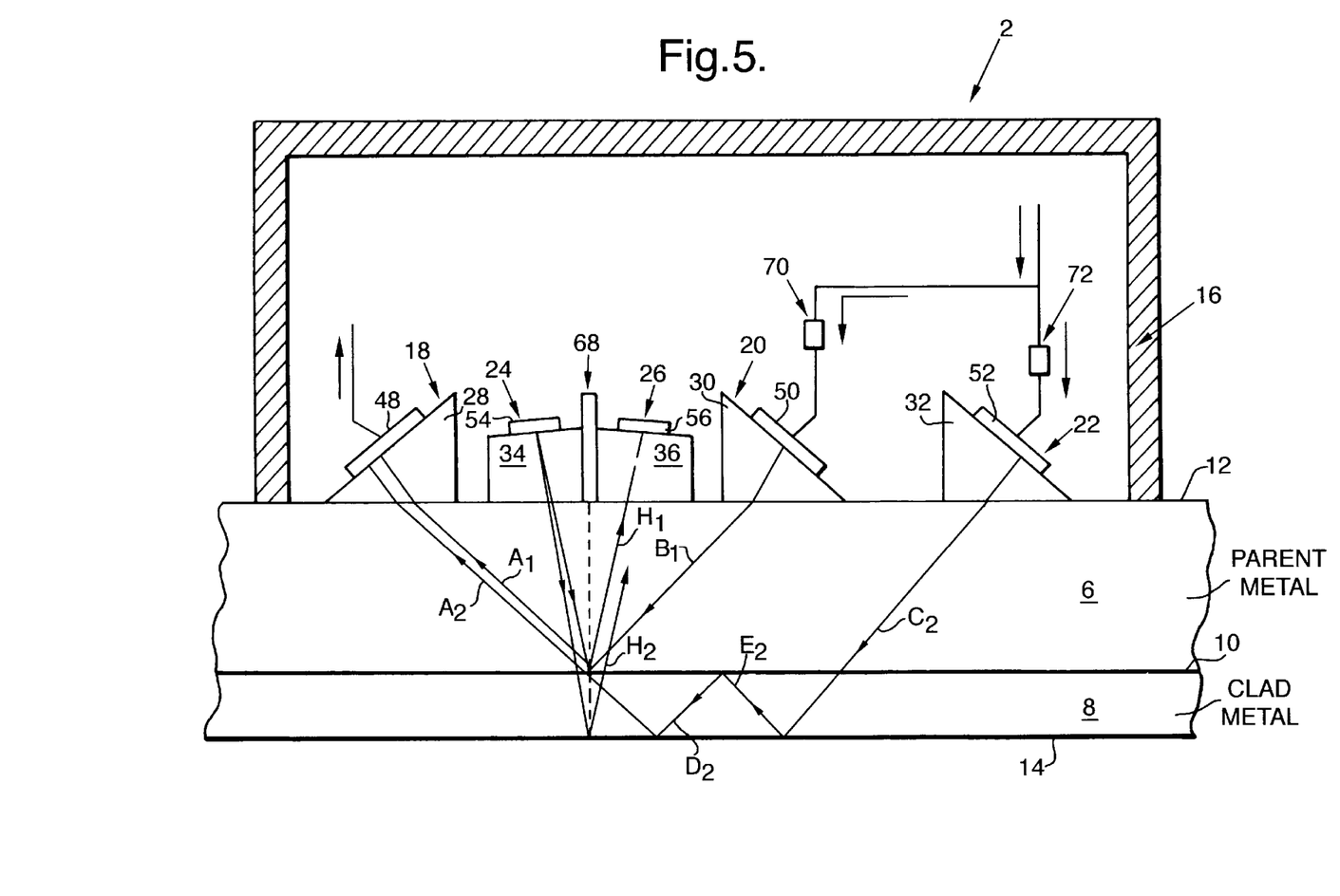
FIG. 5 is a cross-sectional view of a still further embodiment of the device according to the present invention and the mode of performing measurements therewith.

A further modification of operating the device 2 is shown in FIG. 5. In this version, echo signal $A_2$ received by the transducing means 18 is the second reflection of wave $C_2$ from the inner surface 14 of the workpiece. In this case, K=2, and the distance $L_2=4$ h·tan$\alpha$.

Echo signals B and C received by transducing means 20, 22 of FIGS. 2 and 3, or echo signals $A_1$ and $A_2$ received by transducing means of FIG. 4, arrive in the transducing means 22, which acts as the receiver of the device. The clad metal thickness is determined by the difference in times of propagation of echo signals B and C (FIGS. 2 and 3), or $A_1$ and $A_2$ of FIGS. 4 and 5.

Figure 6:
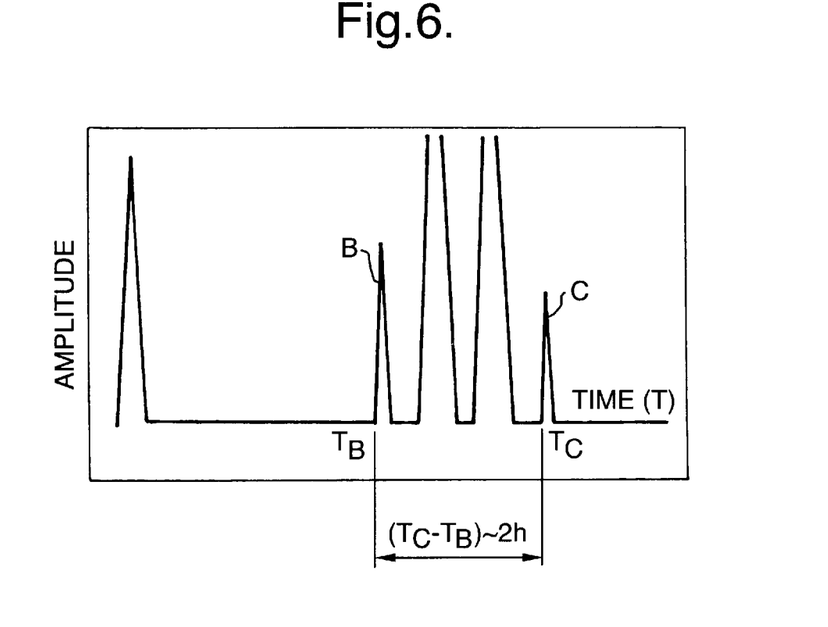
FIGS. 6 and 7 are graphs illustrating the time distribution of reflected signals for embodiments of FIGS. 3 and 5, respectively.

FIG. 6 illustrates the time distribution of shear wave echo signals from the device 2 of FIG. 3. Here, the time at point $T_B$ corresponds to the time of propagation of echo signal B from piezocrystal 48 to piezocrystal 50, and the time at point $T_c$ corresponds to the time of propagation of the echo signal C from piezocrystal 48 to piezocrystal 52. The difference $T_c-T_B$ is directly proportional to twice the thickness (2 h) of the clad metal layer 8.

For the embodiment of FIG. 2, this difference $T_c-T_B$ is directly proportional to the thickness (h) of the clad metal.

Figure 7:
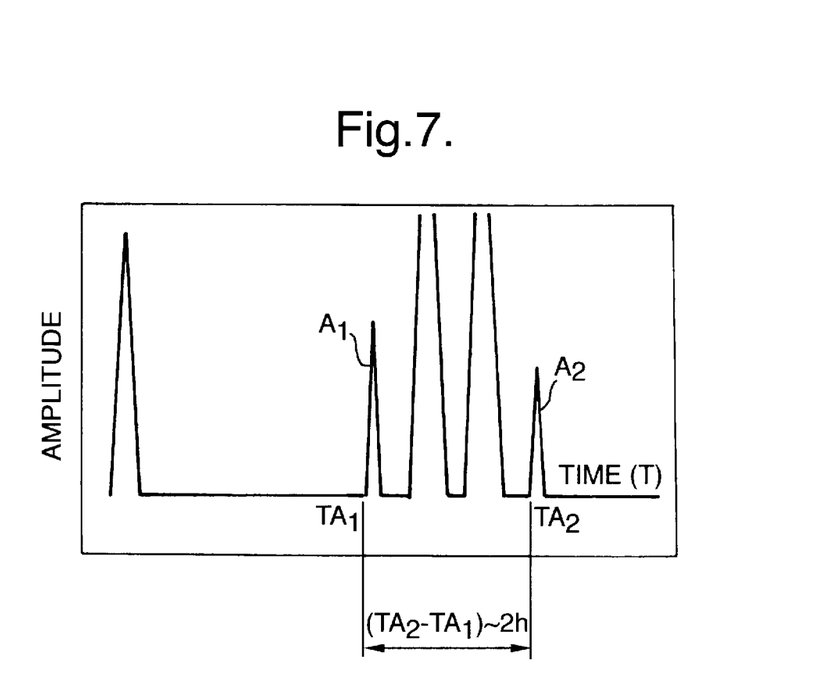

FIG. 7 shows the time distribution of shear wave echo signals from the device 2 according to the embodiment of FIG. 5. Here, the time at point $T_{A1}$ corresponds to the time of the echo signal $A_1$ propagating from piezocrystal 50 to piezocrystal 48, and the time at point $T_{A2}$ corresponds to the time of the echo signal $A_2$ propagating from piezocrystal 52 to piezocrystal 48. The difference $T_{A2}-T_{A1}$ is directly proportional to twice the thickness (2 h) of the clad metal layer 8.

For the version of FIG. 4, the difference $T_{A2}-T_{A1}$ is directly proportional to the clad metal thickness (h).

Along with informative echo signals B, C, $A_1$ and $A_2$, one can observe two or more non-informative signals located between the informative signals on a flaw detector screen. The informative signals B, C, $A_1$ and $A_2$ are always boundary signals.

Figure 8:
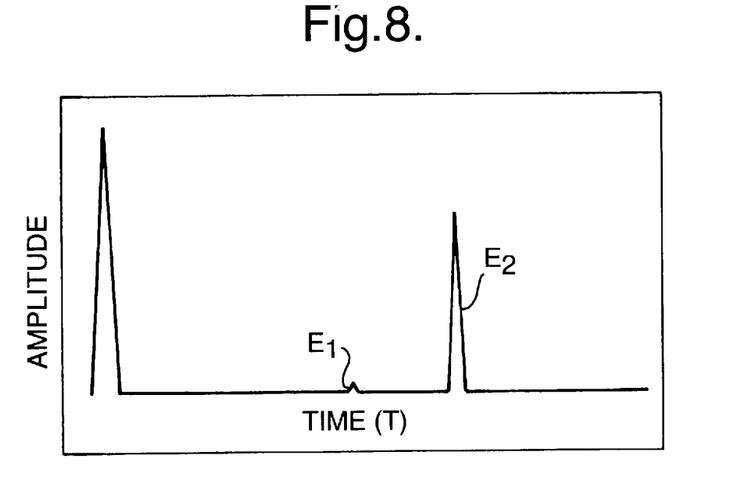
FIGS. 8 and 9 are graphs illustrating the propagation time of signals of longitudinal waves reflected from the boundary surface between the two metals of the workpiece.
Figure 9:
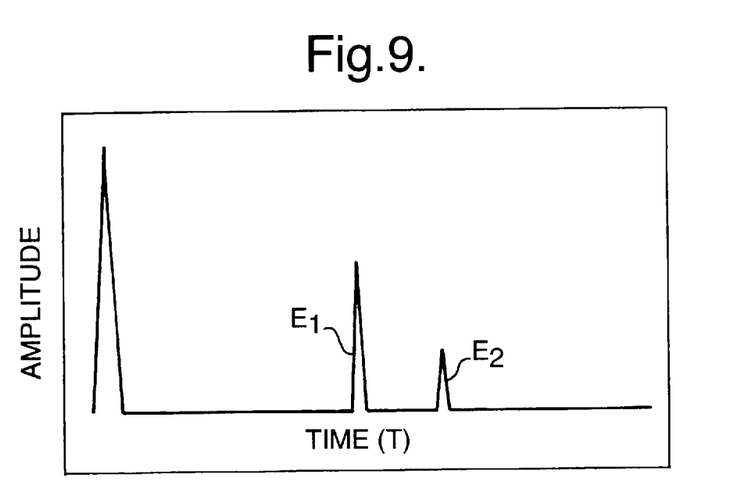

FIGS. 8 and 9 illustrate the propagation time for echo signals of longitudinal waves for, e.g., quality control of the bonding of two metals, with transducer means 24, 26. FIGS. 8 and 9 show the cases of the absence and presence of defects, respectively. The signal $E_1$ (its value being small or negligible) corresponds to the echo signal reflected from the boundary surface of the two metals in the absence of defects, or to the signal reflected from the defect.

Signal $E_2$ corresponds to the echo signal reflected from the inner surface of the workpiece and has a high amplitude in the event of the absence of any defect, and a low amplitude in its presence.

It should be noted that the present invention is directed to a device utilizable for ultrasonic inspection of a multi-layered metal workpiece and not to an entire system for measuring and/or calculating the thickness of the clad metal layer and/or for detecting defects in the welding and/or in the workpiece. Such systems, electrically connected to probes of various types, are per se known, at least from U.S. Pat. No. 5,349,860 mentioned above and from the references cited thereagainst, and do not constitute part of the present invention.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for the ultrasonic inspection of a multilayer metal workpiece consisting of at least one parent metal layer and a clad metal layer, and having an outer surface, at least one boundary surface, and an inner surface, said device comprising:

a housing accommodating at least three spaced-apart, ultrasonic transducing means capable of receiving electrical input signals, initiating transmission of ultrasonic waves to said workpiece, and receiving reflected ultrasonic waves to be transduced into electrical output signals, each of said transducing means being constituted by an acoustic prism having a first face for at least indirectly contacting a workpiece, a second face extending in a plane forming an angle $\alpha$ with the plane of the outer surface of said workpiece, and a piezocrystal attached to said second face, wherein the distance $L_2$ between the points where the acoustic axes of each of the second and the third spaced-apart transducing means of said at least three spaced-apart transducing means traverses the first face of the associated acoustic prism, is determined by the expression:

$$L_2 = K \cdot 2 \ h \cdot \tan \alpha$$

wherein:

K is a coefficient indicating the number of skips of the shear wave reflection from the inner surface of said workpiece, and h is the mean thickness of said clad metal layer.

2. The device as claimed in claim 1, wherein the distance $L_1$, between points where the acoustic axis of each of the first and the second transducing means of said three spaced-apart transducing means traverses the first face of its acoustic prism, is determined by the expression $$L = hd \ 1 = 2 \ H \cdot \tan \alpha$$

wherein: H is the thickness of the mother metal layer.

3. The device as claimed in claim 1, wherein said housing further comprises two juxtaposed transducing means separated by an acoustic screen for transmitting signals into, and receiving echo signals from, said workpiece, wherein said signals are longitudinal waves.

4. The device as claimed in claim 3, wherein said two juxtaposed transducer means are located between the first and second transducing means of said three spaced-apart transducing means, at a position wherein the acoustic axes of said juxtaposed transducer means intersect at the same point where the acoustic axes of said first and second transducing means intersect.

5. The device as claimed in claim 1, wherein the piezocrystals of said second and third transducing means are connected in parallel through control means operating to level echo signals reflected from said workpiece.

6. The device as claimed in claim 1, wherein the first of said three spaced-apart transducing means is operative to transmit shear waves into said workpiece, the second transducing means is operative to receive echo waves reflected from said boundary surface, and the third transducing means is operative to receive echo waves reflected from the inner surface of said workpiece.

7. The device as claimed in claim 1, wherein the first of said three spaced-apart transducing means is operative to receive echo signals reflected from said boundary surface and inner surface of said workpiece, the second transducing means is operative to transmit shear waves into said workpiece to be reflected by said boundary surface, and the third transducing means is operative to transmit shear waves to be reflected from the inner surface of said workpiece.

8. The device as claimed in claim 2, wherein the distances $L_1$ and $L_2$ between said transducing means are calculated to facilitate multiple reflections of transmitted shear waves from said boundary and inner surfaces of said workpiece.

9. The device as claimed in claim 1, wherein said transducing means are affixed inside said housing by epoxy.

\* \* \* \* \*